(12) United States Patent
Berger

(10) Patent No.: US 6,981,974 B2
(45) Date of Patent: Jan. 3, 2006

(54) CANNULATED INTERNALLY THREADED BONE SCREW WITH APERATURED INSERT

(76) Inventor: J. Lee Berger, 895 Mohawk Rd., Franklin Lakes, NJ (US) 07417

( * ) Notice: Subject to any disclaimer, the term of this patent is extended or adjusted under 35 U.S.C. 154(b) by 237 days.

(21) Appl. No.: 10/357,390

(22) Filed: Feb. 4, 2003

(65) Prior Publication Data

US 2003/0120277 A1     Jun. 26, 2003

Related U.S. Application Data

(63) Continuation-in-part of application No. 10/154,923, filed on May 28, 2002, which is a continuation of application No. 09/130,374, filed on Aug. 7, 1998, now Pat. No. 6,436,100.

(51) Int. Cl.
A61B 17/86          (2006.01)

(52) U.S. Cl. .................... 606/73; 606/74; 606/103; 411/397

(58) Field of Classification Search ................. 606/62, 606/65, 66, 72, 73, 74, 103, 232; 411/395, 411/396, 397
See application file for complete search history.

(56) References Cited

U.S. PATENT DOCUMENTS

| | | | |
|---|---|---|---|
| 1,789,060 A | 1/1931 | Weisenbach | |
| 2,121,193 A | 6/1938 | Hanicke | |
| 2,243,717 A | 5/1941 | Moreira | |
| 2,550,866 A | 5/1951 | Rosan | |
| 2,823,574 A | 2/1958 | Rosan | |
| 4,013,071 A * | 3/1977 | Rosenberg | 606/73 |
| 4,155,162 A | 5/1979 | Weissman | |
| 4,295,765 A * | 10/1981 | Burke | 410/101 |
| 4,360,012 A | 11/1982 | McHarrie et al. | |
| 4,858,601 A | 8/1989 | Glisson | |
| 4,878,915 A | 11/1989 | Brantigan | |
| 4,950,270 A | 8/1990 | Bowman et al. | |
| 5,129,906 A | 7/1992 | Ross et al. | |
| 5,169,400 A | 12/1992 | Muhling et al. | |
| 5,217,462 A | 6/1993 | Asnis et al. | |
| 5,423,819 A | 6/1995 | Small et al. | |
| 5,431,651 A | 7/1995 | Goble | |
| 5,456,267 A | 10/1995 | Stark | |
| 5,498,265 A | 3/1996 | Asnis et al. | |
| 5,514,138 A | 5/1996 | McCarthy | |
| 5,549,677 A | 8/1996 | Durr et al. | |
| 5,584,836 A | 12/1996 | Ballintyn et al. | |
| 5,690,633 A | 11/1997 | Taylor et al. | |
| 5,964,767 A * | 10/1999 | Tapia et al. | 606/73 |
| 5,976,139 A | 11/1999 | Bramlet | |

* cited by examiner

Primary Examiner—David O. Reip
(74) Attorney, Agent, or Firm—John S. Hale; Gipple & Hale

(57) ABSTRACT

A bone screw assembly comprising: a bone screw with an externally threaded shank having a head integrally formed at the proximal end and defining a cannula extending through the head and shank. An internal thread formed on the surface defining the inner cannula to receive an anchor bolt having a threaded portion, and a head defining plurality of through-going wire receiving holes.

20 Claims, 4 Drawing Sheets

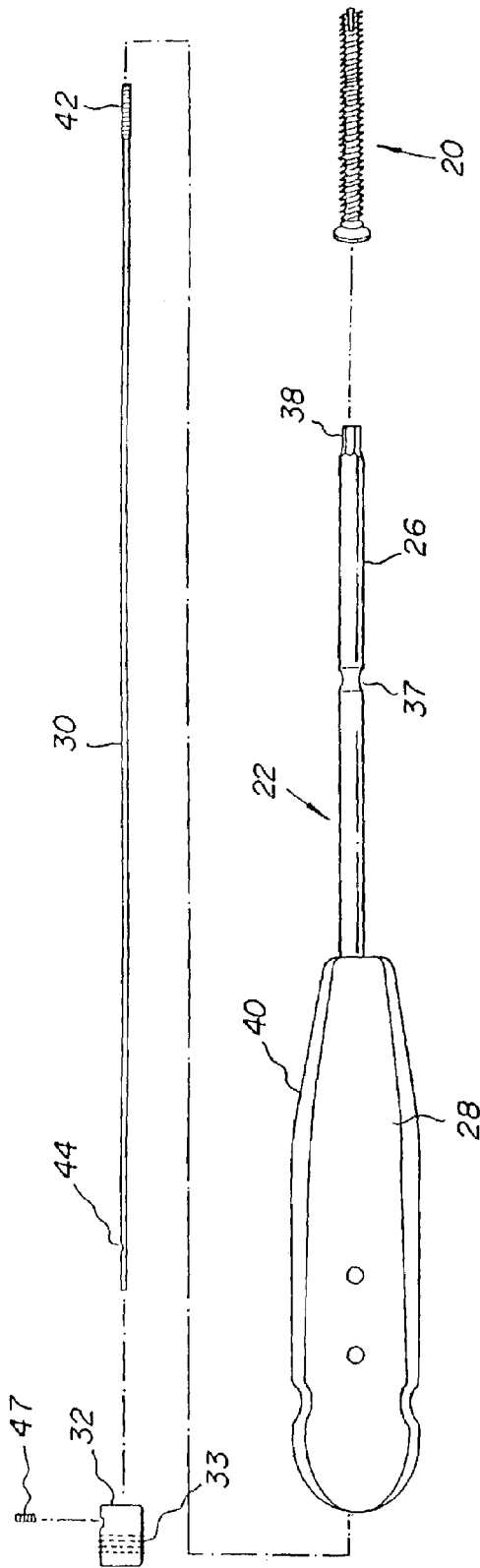
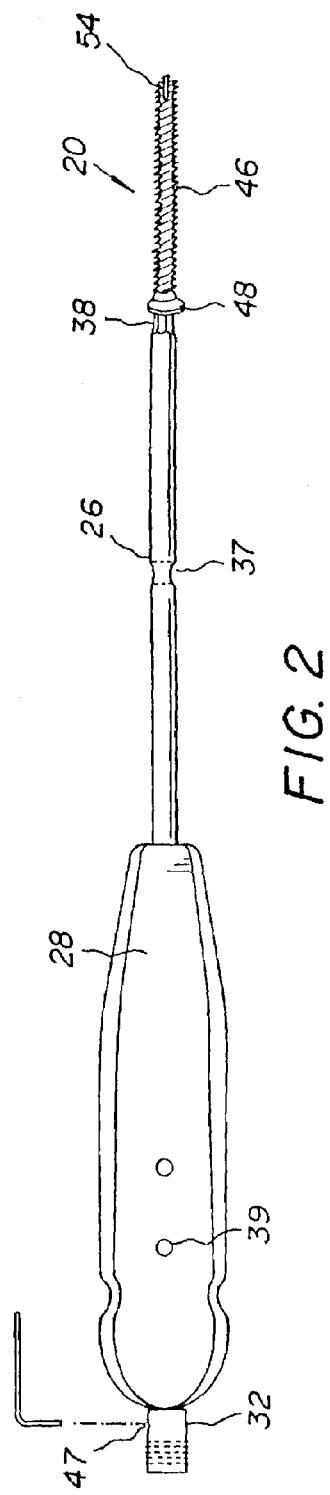
FIG. 1
FIG. 2

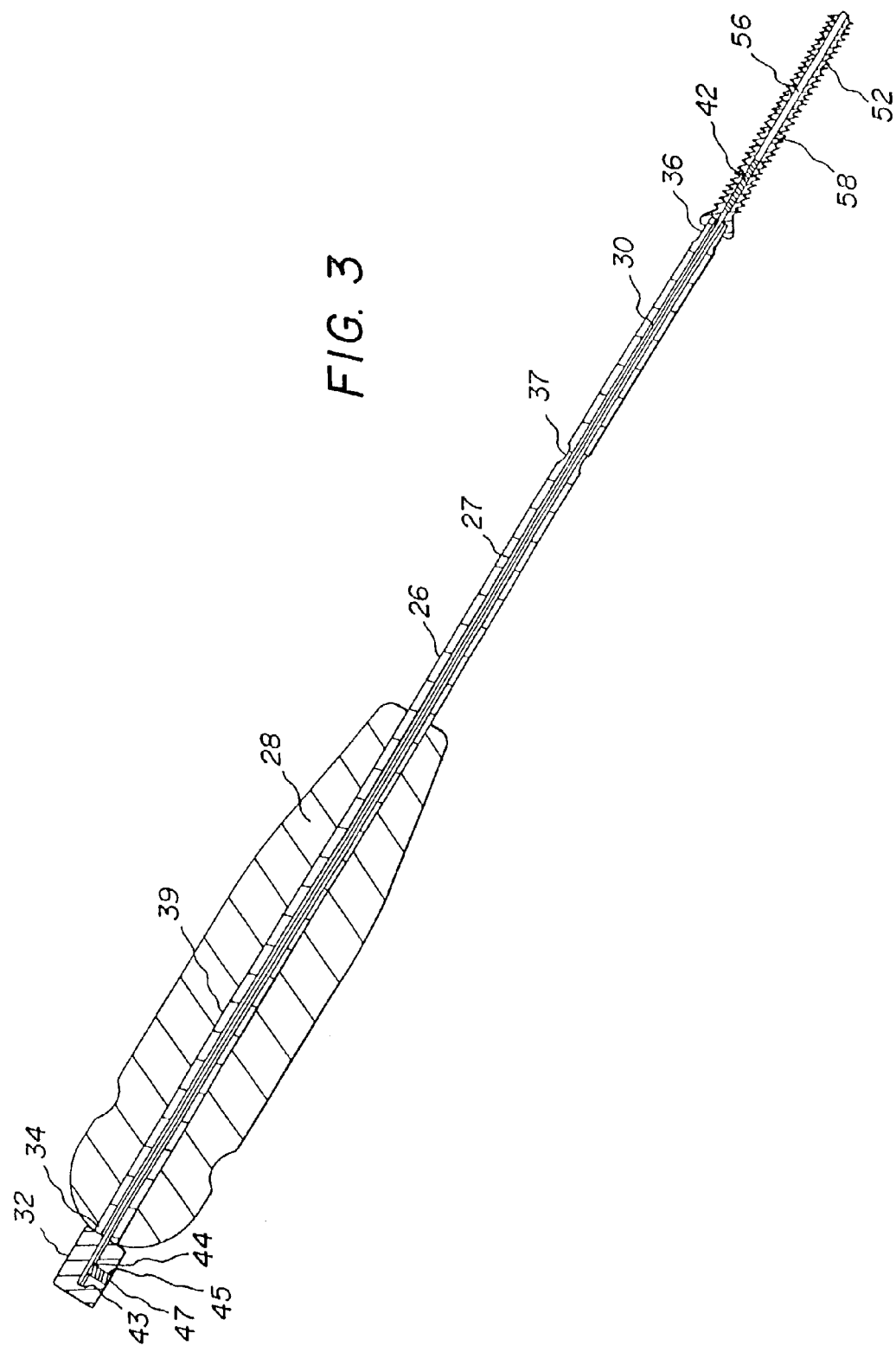

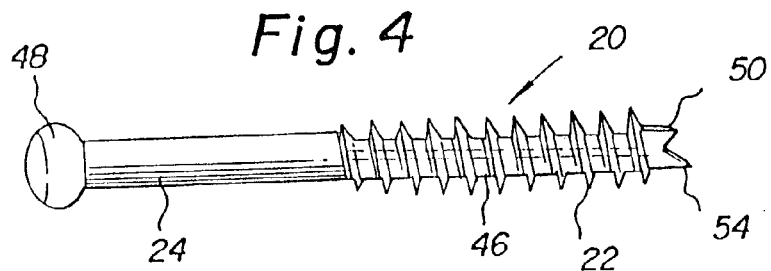
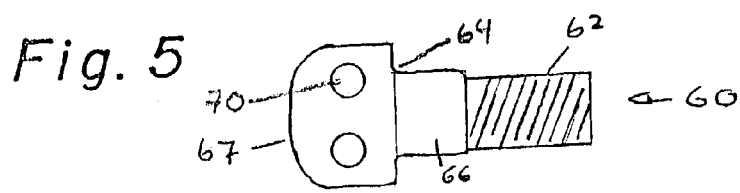
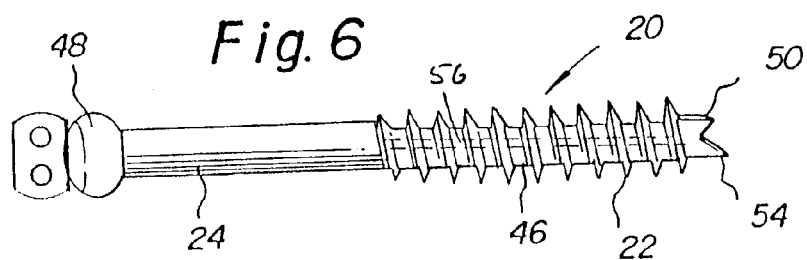
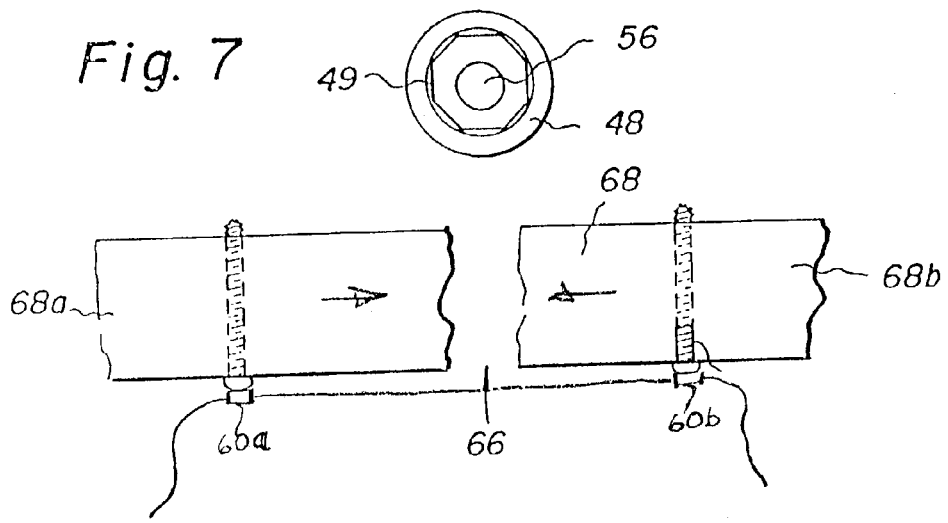

CANNULATED INTERNALLY THREADED BONE SCREW WITH APERATURED INSERT

RELATED APPLICATIONS

This is a continuation-in-part application of U.S. patent application Ser. No. 10/154,923 filed May 28, 2002, which is a continuation application of U.S. patent application Ser. No. 09/130,394 filed Aug. 7, 1998 issued as U.S. Pat. No. 6,436,100.

FIELD OF THE INVENTION

The invention generally relates to bone fracture reduction and fixation and more particularly to a cannulated, internally threaded bone screw having a threaded head with axially aligned bores.

BACKGROUND OF THE INVENTION

It is known to use screw-type devices and associated drivers for bone fracture repair. These screw-type devices may be used in combination with clamps to achieve bone fracture fixation. As one example of same, U.S. Pat. No. 5,498,265 issued Mar. 12, 1996 discloses a bone screw and a driver for driving the screw into a fracture site. The bone screw has a threaded shank having proximal and distal externally threaded shank portions and an internally threaded head sleeve portion which receives the threaded rod of the driver. The driver has a handle and an inner rod connected to the handle. The rod fits within the head sleeve and mates with a cutout in the proximal end of the threaded shank portion. After the screw is placed in a fractured bone, the length of the screw can be adjusted longitudinally to compress the fracture.

U.S. Pat. No. 2,243,717, issued May 27, 1941, for a surgical device shows a cannulated bone screw having a threaded end, a square shaft portion, a round shaft portion and a screw portion. A clamp formed with a head and skirt has a bore allowing it to be mounted on the threaded end. A nut is threadedly mounted on the threaded end of the bone screw. When the bone screw is used in fracture repair, the fracture site is drilled to form a bore and the screw portion of the bone screw is screwed into the bone bore using wrench members specially adapted to drive the bone screw. When the bone screw is firmly anchored in the bone, the guide wire previously inserted is withdrawn, the clamp is applied to the threaded end of the bone screw, and the nut is caused to engage the threaded end. Tightening the nut moves the clamp towards the screw portion to fix the fracture.

An example of a similar screw type device, the length of which can be adjusted to compress a fracture site can be found in U.S. Pat. No. 2,121,193, issued Dec. 21, 1932. U.S. Pat. No. 4,858,601, issued Aug. 22, 1989, is also directed toward a adjustable length screw in the form of a sectioned bone screw which is cannulated and threaded on its outer surface. The bone sections are held together by a spindle received in the cannula and soldered to a section.

Screw-type devices which are used in combination with external clamping means to achieve bone fracture reduction and fixation are also known. U.S. Pat. No. 5,690,633, issued Nov. 25, 1997, shows a fracture fixation device which combines the functions of external fixation pins and external fixation or "lag-type" screws in a single unit. The fracture fixation device includes cannulated screw means for screwing into a first bone fragment over a guide pin and engagement means in the form of a collar mounted on a rod for engaging a second bone fragment. The screw means and engagement means coact to compress first and second bone fragments. Attachment means preferably integral with the screw means has an outer end for attachment to an external fixator system which includes an elongated external fixator rod and at least a pair of external fixator connectors attached to the rod at spaced locations.

Further examples of external fixation devices and clamps can be found in U.S. Pat. No. 1,789,060, issued Jan. 13, 1931, and U.S. Pat. No. 4,360,012, issued Nov. 23, 1982.

A screw and driver for securing a bone block is disclosed in U.S. Pat. No. 5,423,819, issued Jun. 13, 1995. The screw and driver are both rotationally and axially releaseably coupled so the screw can be inserted in a downwardly facing hole. The screw is preferably threaded along its entire exterior surface length and has a blind bore which opens on the proximal end of the screw. A driver with an elongated shaft is inserted into a counterbore portion of the axial blind bore of the screw so that the front portion will compress radially. When the front portion is fully inserted, it snugly engages the wall of the bore with a minor spring biased interference so that the driver is releaseably coupled to the screw. The driver also includes an elongate intermediate portion having a hexagonal cross-section and the counterbore of the screw is provided with a complimentary hexagonal cross-sectional configuration so that rotation of the intermediate portion causes rotation of the screw. In one embodiment of the screw and driver, a throughgoing axially aligned bore is provided in both the screw and the driver to accommodate a K-wire allowing the screw to slide freely along the wire.

U.S. Pat. No. 5,431,651, issued Jul. 11, 1995, shows a cross pin and set screw femoral and tibial fixation apparatus and method for mounting a ligament graft. The patent is directed towards an arthroscopic surgical procedure for replacement of a cruciate ligament in a knee and requires fixation of the ends of a ligament in a prepared tunnel. Transverse holes are drilled in the femoral tunnel during the procedure preferably using a drill guide. The apparatus includes a drill guide for drilling the transverse hole or holes which is arranged to be releasable from a first twist drill so that the first twist drill is left in place to be used for guiding further drilling and for passage of a fastener device. A K-wire or the first twist drill that has been left in place is then used for guiding a second twist drill for enlarging the transverse hole and for guiding a cannulated screw fastener device in the femoral bone end of a ligament graft that has been fitted in to the femoral tunnel section. A set screw is mounted on a forward end of a turning tool and the turning tool and set screw are cannulated to receive a K-wire. A coupling end of the turning tool is seated in a rear end recess in the set screw to mount the screw on the turning tool so that the turning tool and set screw are rotatably coupled but not axially coupled.

A cannulated bone screw is shown in U.S. Pat. No. 4,950,270, issued Aug. 21, 1990. The bone screw has an axial cannula suitable for use with a guide pin for positioning the screw in a bore. The screw is provided with an exterior screw thread having a normal helical winding for screwing insertion of the screw into a bone material. The external threading extends the length of the screw to facilitate the complete insertion of the same in the bone.

A cannulated screw and driver used in bone marrow harvesting and bone biopsy systems is shown in U.S. Pat. No. 5,456,267, issued Oct. 10, 1995. The cannulated screw has a torque receiving head and threaded shaft exterior with one embodiment including inner threads which terminate a hexagonal shaped interior portion. The head is provided with a hexagonal shaped interior portion to permit engagement with a driving tool. The screw includes a structure on one end permitting attachment of a fitting for applying negative pressure to facilitate marrow harvesting. The embodiment includes inner threads on a first end, or in the alternative, pressure fittings or twist lock fittings may be provided. The threads or other structures must provide sufficient seal to permit the negative pressure required for harvesting.

An examination of the prior art indicates the need for a fracture reduction bone screw that provides an attachment site for insertion of wires to act as a fixation point which can be manually manipulated to effect fracture reduction and provide structural support for devices to effect bone fracture fixation.

The use of threaded screw having a suture hole or thread fastening hold therein is know in the prior art. U.S. Pat. No. 5,849,004 issued Dec. 15, 1998 is directed toward an surgical anchor useful in the repair or replacement of ligaments and/or tendons to associated human bone structure and include a threaded insert which screws into a threaded bore formed in the anchor. The insert has a head which defines opposed apertures.

Another U.S. Pat. No. 5,584,835 issued Dec. 17, 1996 discloses a two-part device for suturing soft tissue to bone employs a bone anchor which is installed in the bone and a suture anchor which is coupled to the soft tissue and then engaged with the bone anchor. A side by side suture holder can be used as is seen in FIGS. 2, 12 and 15. The engagement of the suture anchor with the bone anchor is readily reversible so as to permit adjustments in the placement of the sutures.

In addition to the aforenoted patents, U.S. Pat. No. 5,707,394 issued Jan. 13, 1998; U.S. Pat. No. 5,720,7661 issued Feb. 24, 1998; U.S. Pat. No. 5,824,011 issued Oct. 20, 1998; U.S. Pat. No. 6,045,573 issued Apr. 4, 2000; U.S. Pat. No. 6,214,031 issued Apr. 10, 2001; U.S. Pat. No. 6,264,677 issued Jul. 24, 2001; U.S. Pat. No. 6,423,067 issued Jul. 23, 2002; U.S. Pat. No. 6,488,684 issued Dec. 3, 2002 disclose threaded fasteners having throughgoing apertures formed therein for holding sutures and the like.

SUMMARY OF THE INVENTION

The present invention discloses and describes a cannulated, externally and internally threaded bone screw for same for use in the reduction and fixation of bone fractures. An anchor bolt is mounted to the head of the screw is shaped to provide a double apertures which have axis in the same plane to accommodate fixation of orthopaedic equipment.

The internal threading of the bone screw and associated anchor bolt allows the bone screw assembly to be used in a wide range of orthopedic applications. For example, the internal threading can serve as an attachment site for the driving device or the anchor bolt which is used for fixation of orthopedic equipment such as wires, sutures, bone plates, rods or other types of devices.

Because the screw is secured to the driver device by a threaded rod and because the bone screw is constructed of high grade surgical steel with machined external and internal threading, considerable force can be applied to the unit to align the bone, reduce the bone fracture and apply traction to the fracture site. The driver can be quickly detached from the screw by manually rotating the cap member to disengage the rod from the internal screw threading. This allows the bone screw assembly to be used in a wide range of orthopedic applications. The anchor bolt can then be attached which becomes an attachment set for wire fixation.

Yet another object of the invention is to provide a bone screw assembly of simple construction which can be used to apply traction to the fracture site.

It is an object of the invention to provide a self-drilling, self-tapping cannulated bone screw that is both externally and internally threaded. The internal threading can advantageously provide an attachment site for a reduction screw driving device that can be used to drive the internally threaded bone screws into bony tissue including cortical or cancellous bone during orthopedic surgical procedures.

It is a further object of the present invention to provide an internally threaded bone screw that can be used for bone reduction and fixation of fractured bones, for the fixation of orthopedic equipment such as circlage wire.

It is also an object of the invention use the bone screw assembly for potential attachment sites for wire fixation and/or a suture anchors as the pull out strength of the device provides a significant advantage over current suture anchors.

Another object of this invention is to use the bone screw assembly to align and reduce fractures by passing multiple wires through the holes in the head of the assembly;

It is a further object of this invention to show how a plurality of the assemblies can be used for fixation of fractures using external support structures; and to show how a driving device can be easily removed from an assembly once the bone screw is in place and the screw assembly can be used to hold an anchor bolt to hold circlage wires.

These and other objects, advantages, and novel features of the present invention will become apparent when considered with the teaching contained in the detailed disclosure along with the accompanying drawings.

BRIEF DESCRIPTION OF THE DRAWINGS

FIG. 1 is a partially exploded view of the bone reduction and fixation invention showing a driver and cannulated, internally and externally threaded bone screw;

FIG. 2 is a side elevational view of the bone reduction and fixation assembly of FIG. 1;

FIG. 3 is a cross-sectional view of the bone reduction and fixation assembly of FIG. 2;

FIG. 4 is a side elevational view of a partially externally threaded, cannulated and internally threaded bone screw used in the invention;

FIG. 5 is an enlarged side elevational view of a threaded anchor bolt used with the internally threaded bone screw of FIG. 4;

FIG. 6 is side elevational view of the bone screw of FIG. 4 and anchor bolt of FIG. 5 assembled;

FIG. 7 is an enlarged front elevational view of the head of the bone screw of FIG. 4 with the anchor bolt removed;

FIG. 8 is a schematic fragmentary side elevational view of a fracture site showing a plurality of bone reduction and fixation assemblies secured to portions of the fractured bone to reduce the bone fracture prior to insertion of the anchor bolt.

DETAILED DESCRIPTION OF THE PREFERRED EMBODIMENT OF THE INVENTION

Figure 9:
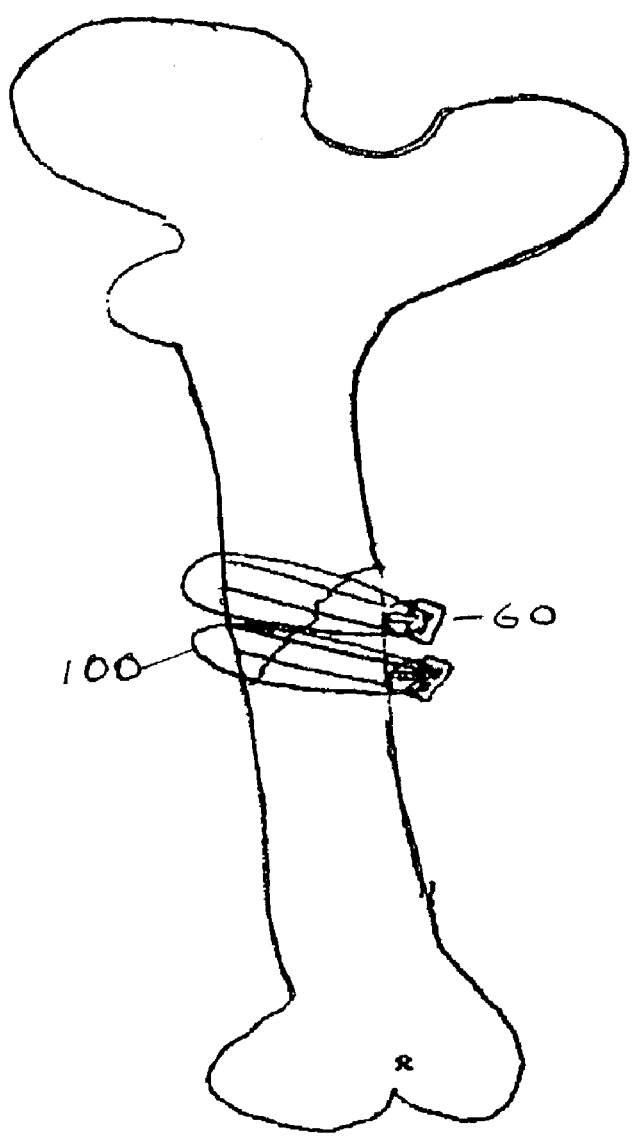
FIG. 9 is a schematic side elevational view showing use of the screw assembly in circlage wire fixation.

The preferred mode and best embodiment of the present invention is shown in FIGS. 4 to 6. Referring now to the drawings, FIGS. 1–3 show a cannulated, internally and externally threaded bone screw 20 and a cannulated driver device 22 constructed according to the principles of the present invention.

The driver device 22 includes a shaft member 26 defining a throughgoing bore 27, a handle 28 and includes a rod 30 and a cap member 32. The rod 30 and cap member 32 are used to releaseably secure the bone screw 20 to the driver device 22 as will later be described. The shaft member 26 is an elongated, generally cylindrical structure which has a cylindrical throughgoing bore or cannula 27 best seen in the cross-sectional view of FIG. 3 which extends longitudinally from a proximal end 34 of the shaft member 26 to a distal end 36.

The shaft member 26 is an integral tubular structure preferably constructed of surgical steel, although any suitable material can be used, and includes a shaped engagement structure 38 integrally formed at the distal end 36 and one or more annular grooves 37 spaced along its length. The engagement structure 38 which preferably has a hexagonal configuration facilitates the mating and rotational engagement of the bone screw 20 with the driver as will be described and the grooves 37 may be used as attachment sites for conventional clamp members during a bone fixation procedure. It will be appreciated that the engagement structure 38 may take any angular configuration such as square, octagonal or the like and can alternatively engage the outer periphery of the screw head.

The handle 28 has a throughgoing bore 39 to receive the proximal end 34 of the shaft member 26 and is preferably constructed of wood or plastic. The handle 28 is secured to the shaft member 26 by securing the handle sections together with conventional rivets 39 or by other suitable means. The rivets do not extend into or through the bore of the shaft member 26. Alternatively, the handle member 28 may be removably mounted to the shaft member 26.

The rod 30 is an integral, solid, generally cylindrical structure preferably constructed of surgical or high grade steel and is provided with a threaded section 42 at its distal end and a machined recess or well 44 near its proximal end which receives set screw 47. The cap member 32 is a generally cylindrical structure that has a blind bore 43 to receive the proximal end of the rod 30 and a cylindrical, internally threaded passage 45 which extends from a side surface of the cap member 32 into the blind bore 43 to permit the passage of a conventional set screw 47 having an Allen head. A conical end portion of the Allen set screw is received within the well 44 in the rod 30 to lock the cap member 32 to the rod 30. The outer surface of cap 32 is knurled at 33 to allow the cap 32 and secured rod 30 to be rotated within bore 27 of the shaft 26 so that threaded end 42 can be screwed into the inner thread 58 of the cannulated bone screw 20.

The outer diameter of the cylindrical rod 30 is less than the inner diameter of the cylindrical bore 27 in the shaft member 26 so that the rod 30 can be easily received therein and pass therethrough. Conversely the threaded end section 42 has threads with an outer diameter greater than the outer diameter of bore 27 so that rod 30 cannot be pulled through the bore 27 of the shaft 26. When the cap member 32 is releaseably locked to the proximal end of the rod 30, cap member 32 prevents a portion of the proximal end of the rod 30 from entering the cannula 27 of the shaft member 26. As best seen in FIG. 3, the rod 30 is longer than the shaft member 26 so that when the cap member 32 is mounted on the rod 30 and the rod 30 is disposed within the cannula or bore 27 of the shaft member 26, the threaded section 42 of the rod 30 extends a predetermined length beyond the distal end 36 of the shaft member 26 to threadedly engage the internal threading 58 of the bone screw 20.

The cannulated, internally threaded bone screw 20 shown in cross-section in a fully threaded embodiment in FIG. 3 is mounted on the driver device 22 and is also shown in FIGS. 4 and 6. The bone screw 20 is an integral structure preferably made of surgical steel and includes a shank 46, a head 48 and a tip portion 50. The shank 46 of the bone screw 20 has an external thread 52 which is helically formed thereabout, and extends from the head 48 to the tip portion 50. The head 48 has a generally larger outer diameter than the shank 46. An internal thread 54 can receive torque from the engagement structure 38 and apply a compressive force to a bone surface or to retain a bone plate against a bone for fracture fixation. The exterior surface of the tip portion can be tapered and provided with a plurality of flutes 54 so that the bone screw is self drilling. The plurality of flutes 54 extend proximally longitudinally from the tip portion 50 and may extend into the shank 46.

A throughgoing internal bore or cannula 56 extends from the head 48 through the shank 46 to the tip portion 50 and is provided with an internal thread 58, preferably throughout its length. As best seen in FIGS. 5 and 6, an anchor bolt 60 is screwed into the internal thread 58. The anchor bolt 60 has a threaded cylindrical shank 62 and a T-shaped head 64 having a cylindrical stem 66 and rectangular head 67 defining two axially aligned throughgoing bores 70 which can receive and hold a circlage wire 100 as shown FIG. 9 or other strands used in holding the bone fracture together. An engagement head 38 is formed in the head 48 of the bone screw 20. The recess 49 is axially aligned with the cannula 56. The walls of the recess 49 preferably have a hexagonal cross-section and define an engagement recess portion of the bone screw 20 as shown in FIG. 7. The engagement structure 38 of the driver device 22 is formed by a hexagonal configuration on the distal end of the shaft 26 and is dimensioned to be received within the recess 49 formed in the head of the bone screw 20 to rotatably engage the bone screw. It is understood that this structure is exemplary only and that the engagement portion of the bone screw may also be formed on the outer periphery of the head portion.

The external surface of body portion 46 of the bone screw 20 is partially threaded at section 22 and smooth surfaced or unthreaded at section 24 and the tip portion 50 is provided with a plurality of flutes 54. The integral head 48 has a larger exterior diameter than the body portion and defines a hexagonal recess 49 which seats the shaft engagement end 38 and the internal threading preferably extends the entire length of the bone screw cannula 56.

The internal and exterior threads of the bone screws 20 and 220 are preferably formed by machining and the internal thread structures may partially or fully cover the wall of the respective interior bores of the bone screws. Each bone screws is self-drilling and self-tapping.

The bone screw 20 and driver device 22 can be assembled using the rod 30 and cap member 32 as shown, for example, in FIGS. 1–3, to form a bone reduction and fixation assembly 60 which can be used to effect bone fraction reduction and fixation.

The engagement structure 38 of the shaft member 26 and the engagement seat 49 of the bone screw 20 are of complimentary size and shape so that the engagement structure 38 can be snugly received within the engagement seat or recess 49 of the bone screw 20 to rotationally lock the driver device 22 with the bone screw 20. When the driver device 22 and bone screw 20 are so engaged, the throughgoing bore 27 of the shaft member 26 is axially aligned with the internally threaded bore 56 of the bone screw 20. The rod 30 is used to releaseably axially secure the bone screw 20 to the driver device 22 by securing the cap member 32 on the rod 30 by tightening the Allen set screw 47 into the recess 44 of the rod member. The threaded section 42 of the rod 30 is threaded on the internal thread 58 projecting from the internal bore 56 of the bone screw 20 and the rod 30 is rotated by manually manipulating the cap member 32 until the bone screw 20 is tightly axially releaseably interlocked to the driver device 22. Reverse rotation will of course unlock the driver device 22 and bone screw 20.

FIG. 8 shows an example of how an internally threaded bone screw can be used as a fracture reduction device at a fracture site 66 in a bone 68. In this example the fracture 66 has separated the bone 68 into two portions 68a and 68b. Two identical bone fracture reduction and fixation assemblies 60a and 60b are secured to the bone portions 68a and 68b, respectively, adjacent the fracture site 66. The description for insertion of a bone screw 20a, 20b is given with reference to assembly 60a; it being understood that bone screw 60b is inserted in the same way.

A guide hole (not shown) is formed in the cortical portion of the bone fragment 68a proximate the fracture site 66. A smooth surgical guide wire or K-wire is inserted in the guide hole. A conventional cannulated surgical drill, optionally used in conjunction with a conventional drill guide, may be used to form a guide hole. The conventional surgical guide wire or K-wire may be inserted in the guide hole through the cannula of the drill before the same is removed therefrom, leaving the guide wire in place.

With the smooth guide wire in place within the guide hole, the cannulated, internally threaded bone screw 20 is inserted over the guide wire with the cannulated driver device 22 to engage two cortices of bone. The threaded rod 30 and the cap member 32 have not been mounted on the cannulated driving device when the guide wire is used to guide the bone screw and driver to the guide hole. After the bone screw 20 is driven into the bone using the driver device 22 the smooth guide wire is removed leaving the bone screw in the bone portion 68a. The engagement end 38 of the driver device 22 is disengaged from the recess or seat 49 of the bone screw 20 and the externally threaded anchor bolt 60 is rotated and tightened into the internal thread of the cannulated screw by manual rotation.

As shown in FIG. 8, a second assembly 60b can be secured to the bone portion 68b using a second internally threaded bone screw 20b by repeating this procedure. The surgeon can then manipulate the bone portions 68a, 68b and pulling each towards each other to reduce the fracture 66 manually and the anchor bolts 60 can be wired together holding the fracture together.

FIG. 9 shows that the internally threaded bone reduction screw can be applied to a fractured bone allowing the threaded anchor bolt to be attached thereto. By attaching the wires directly through the anchor bolt that is screwed into the bone screw and around the fracture. Wire slippage is reduced and a stronger and more accurate form of fixation with circlage wires can be obtained. This system is superior to traditional circlage wires including the Dall Miles system.

The internally threaded screw can be used independently as bone anchor. It is understood that the bone screws shown herein are exemplary only and not intended to be limiting. One skilled in art will appreciate that the internally threaded cannulated screws can be manufactured in various shapes and sizes and that the internal threads may partially or fully encompass the length of the bone screws.

In the foregoing description, the invention has been described with reference to a particular preferred embodiment, although it is to be understood that specific details shown are merely illustrative, and the invention may be carried out in other ways without departing from the true spirit and scope of the following claims:

I claim:

1. A cannulated torque receiving bone screw assembly comprising:

a screw with an elongated cylindrical shank defining an inner throughgoing cylindrical bore and having a proximal end, a head integrally formed at the proximal end, a distal end, and an outer surface, an engagement structure defined by said head is shaped to receive and rotatably engage a driver having a shape complimentary to the shape of the engagement structure; an external thread is formed on said shank outer surface and extends along a section of said shank. the rest of the outer surface being unthreaded and an internal thread is formed on a surface defining an inner cylindrical bore axially aligned with said shank and a threaded anchor bolt is mounted to said screw adjacent said screw head, said anchor bolt defining at least one throughgoing bore therein transverse the axis of said inner cylindrical bore.

2. A cannulated torque receiving bone screw as claimed in claim 1 wherein said head defines a geometrically shaped recess which is axially aligned with said throughgoing inner cylindrical bore.

3. A cannulated torque receiving bone screw as claimed in claim 1 wherein said anchor bolt comprises a threaded shank and a head which is larger than said shank, said head defining a plurality of throughgoing bores.

4. A cannulated torque receiving bone screw as claimed in claim 3 wherein said plurality of throughgoing bores are positioned parallel to each other and are positioned on opposite sides of an axis taken along said threaded shank of said anchor bolt.

5. A cannulated torque receiving bone screw as claimed in claim 3 wherein said head is T-shaped with a cylindrical stem which is sized to fit into a bore formed in said screw head.

6. A cannulated torque receiving bone screw as claimed in claim 3 wherein said anchor bolt shank is threaded on its outer surface and is of a diameter such that it can be threaded in said internal thread of said bone screw.

7. A cannulated torque receiving bone screw as claimed in claim 3 wherein said head is T-shaped with a cylindrical stem and a substantially rectangular head with planar side surface.

8. A cannulated torque receiving bone screw as claimed in claim 7 wherein said substantially rectangular head has a planar top surface with rounded ends and two parallel bores cut therethrough.

9. A cannulated torque receiving bone screw as claimed in claim 7 wherein said substantially rectangular head has a planar top surface with beveled ends and two parallel bores cut therethrough.

10. A cannulated torque receiving bone screw assembly comprising:

a screw with an elongated cylindrical shank defining a throughgoing cylindrical bore and having a proximal end, a head integrally formed at the proximal end, a distal end, and an outer surface, an engagement structure defined by said head is shaped to receive and rotatably engage a driver having a shape complimentary to the shape of the engagement structure; an external thread is formed on said shank outer surface and an internal thread is formed on a surface defining an inner cylindrical bore and a threaded anchor bolt mounted to said screw adjacent said screw head, said anchor bolt defining a plurality of throughgoing bores; said anchor bolt comprising a threaded shank adapted to be threadedly mounted in said internal thread of said inner cylindrical bore and a T-shaped head, said head defining a plurality of aligned throughgoing bores.

11. A cannulated torque receiving bone screw as claimed in claim 10 wherein said plurality of throughgoing bores are positioned parallel to each other and are positioned on opposite sides of an axis taken along said threaded shank of said anchor bolt.

12. A cannulated torque receiving bone screw as claimed in claim 10 wherein said head is T-shaped with a cylindrical stem which is sized to fit into a bore formed in said screw head.

13. A cannulated torque receiving bone screw as claimed in claim 10 wherein said head is T-shaped with a cylindrical stem and a substantially rectangular head with planar side surface.

14. A cannulated torque receiving bone screw as claimed in claim 10 wherein said substantially rectangular head has a planar top surface with rounded ends and two parallel bores cut therethrough.

15. A cannulated torque receiving bone screw as claimed in claim 10 wherein said substantially rectangular head has a planar top surface with beveled ends and two parallel bores cut therethrough.

16. A cannulated torque receiving bone screw assembly comprising:
a screw with an elongated cylindrical shank defining a throughgoing cylindrical bore and having a proximal end, a head integrally formed at the proximal end, a distal end, and an outer surface, an engagement structure defined by said head is shaped to receive and rotatably engage a driver having a shape complimentary to the shape of the engagement structure; an external thread is formed on said shank outer surface and an internal thread is formed on a surface defining an inner cylindrical bore and a threaded anchor bolt selectively threadably mounted to said screw adjacent said screw head, said anchor bolt defining a plurality of throughgoing bores;
said anchor bolt comprising a threaded shank with a planar distal end, the shank being adapted to be threadedly mounted in said internal thread of said inner cylindrical bore, a T-shaped head integrally formed with said shank, said T-shaped head comprising a cylindrical stem which is axially aligned with said shank and a cross piece mounted on the proximal end of said cylindrical stem, said cross piece defining a plurality of aligned througbgoing bores which run at an angle to the central axis of said anchor bolt shank.

17. A cannulated torque receiving bone screw as claimed in claim 16 wherein said cross piece is substantially rectangular with a planar top surface having rounded end surfaces and bores are parallel.

18. A cannulated torque receiving bone screw assembly for treatment of bone fractures comprising:
a screw with an elongated cylindrical shank defining an inner throughgomg cylindrical bore and having a proximal end, a head integrally formed at the proximal end, a distal end, and an outer surface, an engagement structure defined by said head is shaped to receive and rotatably engage a driver having a shape complimentary to the shape of the engagement structure; an external thread is formed on said shank outer surface and an internal thread is formed on a surface defining an inner cylindrical bore axially aligned with said shank and a threaded anchor bolt is mounted to said screw adjacent said screw head, said anchor bolt having a threaded shank and an integral head which is larger than said shank, said head defining a plurality of throughgoing bores transverse the axis of said inner cylindrical bore.

19. A cannulated torque receiving bone screw as claimed in claim 18 wherein said external thread formed on the outer surface of said shank extends along the entire shank.

20. A cannulated torque receiving bone screw as claimed in claim 18 wherein said internal thread formed on a surface defining the bore of said shank extends the length of said bore.

* * * * *